United States Patent [19]

Chiodini et al.

[11] Patent Number: 5,719,122
[45] Date of Patent: Feb. 17, 1998

[54] PHARMACEUTICAL COMPOSITIONS CONTAINING A CALCITONIN

[75] Inventors: Laura Chiodini, Busto Arsizio; Teodoro Fonio, Arese; Gianfranco Rancati, Binasco, all of Italy

[73] Assignee: SmithKline Beecham Farmaceutici S.p.A., Milan, Italy

[21] Appl. No.: 416,874

[22] PCT Filed: Oct. 15, 1993

[86] PCT No.: PCT/EP93/02874

§ 371 Date: Jun. 19, 1995

§ 102(e) Date: Jun. 19, 1995

[87] PCT Pub. No.: WO94/08622

PCT Pub. Date: Apr. 28, 1994

[30] Foreign Application Priority Data

Oct. 20, 1992 [IT] Italy ................. MI92A2400

[51] Int. Cl.$^6$ ................................ A61K 37/30
[52] U.S. Cl. ................ 514/9; 514/2; 514/966; 514/808; 424/433; 424/436
[58] Field of Search ................ 514/2, 9, 808, 514/966; 424/433, 436

[56] References Cited

U.S. PATENT DOCUMENTS 5,430,021   7/1995   Rudnic et al. ................. 514/14

FOREIGN PATENT DOCUMENTS 535 827 A1   4/1993   European Pat. Off. .
2 312 260   12/1976   France .

OTHER PUBLICATIONS

WPIDS abstract 81-80457D JP56118013, Sep. 16, 1981.
WPIDS abstract 91-214557 US5002771 Feb. 3, 1989.
The Merck Manual 15th edition, 1987, pp. 1295-1297, 1644, 2309, 1729, 2657-58.

Primary Examiner—Rebecca Cook
Attorney, Agent, or Firm—Dara L. Dinner; Stephen Venetianer; Edward T. Lentz

[57] ABSTRACT

Pharmaceutical compositions comprising a calcitonin and a polyglycolysed glyceride and a method of enhancing the transdermal or transmucosal absorption of calcitonin in a mammal are disclosed.

21 Claims, No Drawings

PHARMACEUTICAL COMPOSITIONS CONTAINING A CALCITONIN

This application is a 371 of PCT/EP93/02874.

The present invention relates to novel pharmaceutical compositions containing calcitonins, and to a novel method of enhancing the absorption of a calcitonin across a mucosal membrane.

The calcitonins are a class of pharmacologically active peptides, of both natural and synthetic origin, which contain approximately thirty two amino acids, and which have the ability to regulate serum calcium levels.

Various calcitonins, including e.g. natural human, salmon and eel calcitonins and the synthetic eel calcitonin analogue elcatonin are now commercially available and commonly employed, e.g. in the treatment of Paget's disease, Sudeck's disease and osteoporosis.

A considerable and well known problem with the administration of peptides is that they are susceptible to rapid acid and enzyme-induced degradation when administered orally. For this reason, parenteral administration has been, hitherto, the most widely used means of administration and, in the case of peptides of higher molecular weight, such as the calcitonins, has been the only significant effective means of administration.

It is widely recognised that administration by injection can be both inconvenient and unpleasant for the patient, particularly when the administration has to be repeated at regular intervals for long periods, e.g. in the treatment of post-menopausal osteoporosis with calcitonins. Thus, there has been growing interest in the administration of peptides by more acceptable non-invasive alternative routes, for example in the form of sublingual tablets, suppositories, intrapulmonary powders, intranasal drops, sprays, powders, gels, ointments and inserts.

A significant problem with many peptides, particularly those of higher molecular weights, is that they are only poorly absorbed across biological membranes, e.g. mucosal membranes, and thus the bioavailability of the peptide is often very low. Considerable research has therefore been carried out in order to find methods of improving the transepithelial absorption of peptides. One approach is to use an adjuvant or absorption enhancer and there are numerous published reports of compounds which are claimed to have peptide absorption-enhancing properties.

Thus, for example, choline esters (EP 214898), acyl carnitines (EP 215697), aldoses and glucosamines (Japanese Pat. Appl. No. 61 126034), ascorbates and salicylates (EP 37943), alpha-cyclodextrin (EP 0094157), pyroglutamate esters (EP 173990), chelating agents U.S. Pat. No. 4,476, 116) ethanol, benzyl alcohol and polyethylene glycol 400 (EP 371010) have been proposed as absorption enhancers.

There are many published reports that surfactants can enhance the absorption of polypeptides, see for example EP 115627 (Armour), GB 2,127,689 (Sandoz), U.S. Pat. No. 4,548,922 (Carey et al) and Hirai et al., Int. J. Pharm., 9, 165–184, 1981. However, a recognised problem with surfactant absorption promoters is that, they can cause irritation and histolesion at the site of administration. In some cases this may depend upon the amount employed. These problems become of great importance when the peptide is administered regularly over a prolonged period.

We have now found that absorption of elcatonin following rectal administration is surprisingly enhanced when it is administered as a formulation with a polyglycolysed glyceride, and that such formulations do not cause irritation or histolesion. We have also found a surprising enhancement in absorption when elcatonin is administered as a formulation with a polyglycolysed glyceride, to the colonic mucosa.

In a first aspect therefore the present invention provides a composition containing a calcitonin, a polyglycolysed glyceride and a pharmaceutically acceptable carrier.

The invention also provides a method of enhancing the absorption of a calcitonin across a mucosal membrane, which method comprises co-administering with the calcitonin an effective amount of an absorption enhancer which is a polyglycolysed glyceride.

The polyglycolysed glycerides according to the invention may be saturated or unsaturated. Saturated polyglycolysed glycerides are obtainable by partial alcoholysis of hydrogenated vegetable oil with polyethylene glycol or by esterification of saturated fatty acids with polyethylene glycol and glycerol. Unsaturated polyglycolysed glycerides may be obtained by partial alcoholysis of non-hydrogenated vegetable oil with polyethylene glycol.

Polyglycolysed glycerides which may be employed in the invention include saturated polyglycolysed glycerides consisting of $C_8$-$C_{18}$ glycerides and polyethylene glycol esters, such as those available under the wade names Gelucire®, e.g. Gelucire®33/01, 35/10, 37/02 or 44/14; and Labrafil® e.g. Labrafil® WL 2514 CS; unsaturated polyglycolysed glycerides consisting of $C_{16}$-$C_{20}$ glycerides and polyethylene glycol esters such as those available under the wade name Labrafil® e.g. Labrafil® WL 2609 BS, or M 2125 CS; and saturated polyglycolysed $C_8$-$C_{10}$ glycerides, such as those available under the trade name Labrasol. If desired a mixture of polyglycolysed glycerides may be employed. Particularly preferred polyglycolysed glycerides for use in the present invention include Gelucire 44/14 and Labrasol.

The polyglycolysed glyceride comprises 5 to 100% e.g. 5 to 50% by weight of the total excipients. Thus it may be used as the sole carrier for the calcitonin, or may be admixed with other excipients. It will be appreciated that in view of its potency the weight of calcitonin in the formulation is very low relative to the weight of excipients.

The term calcitonin as used herein is intended to refer to that class of pharmacologically active polypeptides including not only naturally occurring calcitonins but also various derivatives and analogues thereof, e.g. in which one or more of the amino acid residues or sequences naturally present is omitted, replaced, reversed or otherwise derivatised or in which the N or C terminal is modified.

The general term calcitonin, as used hereinafter, is intended to mean all such calcitonins whether naturally occurring or synthetic.

Examples of naturally occurring calcitonins include: human calcitonin, Chemical Abstract Service Registry Number (CAS RN)=21215-62-3, which has the structure:

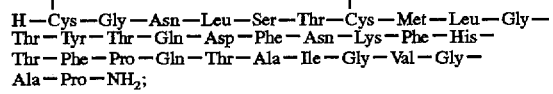

rat calcitonin (CAS RN=11118-25-5) which has the structure:

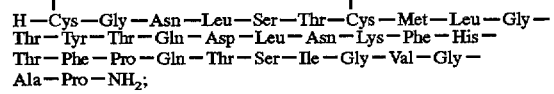

salmon calcitonin (CAS RN=47931-85-1) which has the structure:

```
┌─────────────────────────────────────────────┐
H—Cys—Ser—Asn—Leu—Ser—Thr—Cys—Val—Leu—Gly—
Lys—Leu—Ser—Gln—Glu—Leu—His—Lys—Leu—Gln—
Thr—Tyr—Pro—Arg—Thr—Asn—Thr—Gly—Ser—Gly—
Thr—Pro—NH₂;
``` eel calcitonin (CAS RN=57014-02-5) which has the structure:

```
┌─────────────────────────────────────────────┐
H—Cys—Ser—Asn—Leu—Ser—Thr—Cys—Val—Leu—Gly—
Lys—Leu—Ser—Gln—Glu—Leu—His—Lys—Leu—Gln—
Thr—Tyr—Pro—Arg—Thr—Asp—Val—Gly—Ala—Gly—
Thr—Pro—NH₂;
``` reduced chicken calcitonin I (CAS RN=96157-98-1) which has the structure:

```
┌─────────────────────────────────────────────┐
H—Cys—Ala—Ser—Leu—Ser—Thr—Cys—Val—Leu—Gly—
Lys—Leu—Ser—Gln—Glu—Leu—His—Lys—Leu—Gln—
Thr—Tyr—Pro—Arg—Thr—Asp—Val—Gly—Ala—Gly—
Thr—Pro—NH₂;
``` chicken calcitonin II (CAS RN=103468-65-1) which has the structure:

```
H-gamma-Glu—Cys—Gly—OH        H-gamma-Glu—Cys—Gly—OH
            |                              |
       H—Cys—Ala—Ser—Leu—Ser—Thr—Cys—Val—
Leu—Gly—Lys—Leu—Ser—Gln—Glu—Leu—His—Lys—Leu—
Gln—Thr—Tyr—Pro—Arg—Thr—Asp—Val—Gly—Ala—Gly—
Thr—Pro—NH₂;
``` ox calcitonin (CAS RN=26112-29-8) which has the structure:

```
┌─────────────────────────────────────────────┐
H—Cys—Ser—Asn—Leu—Ser—Thr—Cys—Val—Leu—Ser—
Ala—Tyr—Trp—Lys—Asp—Leu—Asn—Asn—Tyr—His—
Arg—Phe—Ser—Gly—Met—Gly—Phe—Gly—Pro—Glu—
Thr—Pro—NH₂;
``` pig calcitonin (CAS RN=12321-44-7) which has the structure:

```
┌─────────────────────────────────────────────┐
H—Cys—Ser—Asn—Leu—Ser—Thr—Cys—Val—Leu—Ser—
Ala—Tyr—Trp—Arg—Asn—Leu—Asn—Asn—Phe—His—
Arg—Phe—Ser—Gly—Met—Gly—Phe—Gly—Pro—Glu—
Thr—Pro—NH₂; and
``` sheep calcitonin (CAS RN=40988-57-6) which has the structure:

```
┌─────────────────────────────────────────────┐
H—Cys—Ser—Asn—Leu—Ser—Thr—Cys—Val—Leu—Ser—
Ala—Tyr—Trp—Lys—Asp—Leu—Asn—Asn—Tyr—His—
Arg—Tyr—Ser—Gly—Met—Gly—Phe—Gly—Pro—Glu—
Thr—Pro—NH₂.
```

Examples of calcitonins wherein one or more amino acids have been omitted are the des-[Ser², Tyr²²]-Gly⁸-calcitonins described in U.S. Pat. No. 4,597,900 and the des-[Tyr²²]-salmon calcitonin described in U.S. Pat. No. 4,304,692.

Examples of calcitonins wherein the naturally occurring sequence has been modified include the 1,7-dicarbacalcitonins such as eel 1,7-dicarbacalcitonin (elcatonin CAS RN=60731-46-6) which has the structure:

```
         ┌──────── (CH₂)₅ ────────┐
CO—Ser—Asn—Leu—Ser—Thr—NH—CH—CO—Val—Leu—
Gly—Lys—Leu—Ser—Gln—Glu—Leu—His—Lys—Leu—Gln—
Thr—Tyr—Pro—Arg—Thr—Asp—Val—Gly—Ala—Gly—
Thr—Pro—NH₂;
``` salmon 1,7-dicarbacalcitonin (CAS RN=60864-37-1) which has the structure:

```
         ┌──────── (CH₂)₅ ────────┐
CO—Ser—Asn—Leu—Ser—Thr—NH—CH—CO—Val—Leu—
Gly—Lys—Leu—Ser—Gln—Glu—Leu—His—Lys—Leu—Gln—
Thr—Tyr—Pro—Arg—Thr—Asn—Thr—Gly—Ser—Gly—
Thr—Pro—NH₂; and
``` human 1,7-dicarbacalcitonin (CAS RN=66811-56-1) which has the structure:

```
         ┌──────── (CH₂)₅ ────────┐
CO—Gly—Asn—Leu—Ser—Thr—NH—CH—CO—Met—Leu—
Gly—Thr—Tyr—Thr—Gln—Asp—Phe—Asn—Lys—Phe—His—
Thr—Phe—Pro—Gln—Thr—Ala—Ile—Gly—Val—Gly—
Ala—Pro—NH₂.
```

In the context of the present invention, a particularly preferred calcitonin is elcatonin (CAS RN=60731-46-6). The preparation and properties of elcatonin and related 1,7-dicarbacalcitonins are described in British Patent Number 1,516,947 (Toyo Jozo).

Another preferred calcitonin is naturally occurring eel calcitonin (CAS RN=57014-02-5). The preparation and properties of eel calcitonin are described in U.S. Pat. No. 3,988,309 (Matsuda et al).

The compositions of the present invention suitably can be administered by methods known in the art for transmucosal and transdermal delivery of pharmacologically active substances. The compositions can be administered to, for example, the rectal, vaginal, nasal, sublingual, buccal, and colonic mucosa and to the skin. They can take the form of drops, aerosols, tablets, capsules, enterically coated solid oral compositions, wafers, gels, ointments, inserts, suppositories, pessaries, patches and membranes.

Particular compositions are those intended for administration to the rectal and vaginal mucosa. When the composition is intended for application to the rectal or vaginal mucosa particular dosage forms include pessaries, suppositories, solutions, foams, suspensions, gels, ointments, tablets and soft gelatin capsules.

Compositions for rectal or vaginal administration are generally presented as a solid suppository or a semisolid or liquid formulation filled into a soft gelatin capsule. It will be appreciated therefore that the excipients for use in such suppository or capsule formulations will be selected and if necessary admixed to give a formulation of the desired consistency at room and body temperatures. Thus, the suppository base may for example comprise one or more components selected from an oil, a fat and a polyethylene glycol which can be admixed with the polyglycolysed glyceride. The oil and/or fat preferably comprises one or more triglycerides as the main component, such as coconut oil, fractionated coconut oil (e.g. Miglyol) palm kernel oil, palm fat, cocoa butter or lard. Examples of hard fat suppository bases include Witepsol, and Suppocire. For use in a capsule formulation the polyethylene glycol component is preferably liquid at room temperature such as polyethylene glycol-200, 300, 400 or 600, whereas for a solid suppository a polyethylene glycol of higher molecular weight is preferred. The relative proportions of the excipients will of course depend inter alia on the consistency of the formulation required. If desired the polyglycolysed glyceride may be employed as the sole carrier in a capsule formulation.

Compositions adapted for rectal administration as described above are particularly preferred.

Also preferred are compositions which deliver the active ingredient to the colonic mucoso. These include enterically coated compositions intended for oral administration, which may for example take the form of a capsule coated with a coating agent which ensures passage of the calcitonin through the stomach its subsequent release preferably in the colon. Suitable coating agents include anionic polymers such as acrylic acid/methacrylic acid ester copolymers (e.g. Eudragit S). Alternatively the formulation may be incorporated in a controlled release delivery form such as that described in WO 90/09168. Excipients which may be incorporated in such enteric capsules or controlled release forms include for example those described above for rectal and vaginal formulations.

When the composition is intended for delivery to the nasal mucosa, particular dosage forms are solutions, aerosols, drops, and gels.

Particular dosage forms for buccal and sublingual administration are gels, suspensions, tablets, patches, ointments, solutions, aerosols and wafers.

Aerosol formulations typically comprise a solution or fine suspension of the active substance in a physiologically acceptable aqueous or non-aqueous solvent and are usually presented in single or multidose quantities in a sealed container. The sealed container can take the form of a cartridge or refill for use with an atomising device, or it can take the form of a unitary dispensing device such as a single dose nasal inhaler (see French Patent Application FR 2578426) or an aerosol dispenser fitted with a metering valve and which is intended for disposal once the contents of the container have been exhausted. Where the dosage form comprises an aerosol dispenser, it will contain a propellant which can be a compressed gas such as compressed air or an organic propellant such as a fluorochlorohydrocarbon. Such aerosol dispensers are well known in the art. The aerosol dosage forms can also take the form of a pump-atomiser and such forms are also well known in the art. The atomising or dispensing devices for dispensing aerosol sprays typically are designed to dispense particles of a size greater than 10 micrometres. In order to ensure that significant quantities of the composition remain in contact with the oral or nasal mucosa, and are not inhaled, the particles suitably are approximately 10–160 micrometres in size.

When the composition is intended to be administered as a liquid spray, the viscosity of the liquid composition can be adjusted as necessary according to known methods to ensure that the composition is sprayable.

Compositions in the form of wafers may be for example as described in PCT/GB91/00651. Such wafers are formed substantially of starch and suitably have a thickness of from 0.3 to 1.0 mm.

The compositions according to the present invention may also contain an aqueous or physiologically acceptable non-aqueous solvent or liquid carrier. Examples of non-aqueous solvents or carriers are alcohols, particularly polyhydroxy alcohols such as propylene glycol and glycerol, and vegetable and mineral oils. Such non-aqueous solvents or carriers can if desired be admixed with water to form for example emulsions.

The formulations of the present invention may also contain excipients such as antioxidants, stabilisers, preservatives (e.g. parabens or benzyl alcohol), surfactants e.g. sodium lauryl sulphate, agents for adjusting viscosity, agents for adjusting tonicity (e.g. sodium chloride, glycine or mannitol), and buffering agents.

The compositions may also contain glycyrrhizinic acid or a salt thereof, e.g. sodium or potassium glycyrrhizinate or ammonium glycyrrhizinate. The concentration of the glycyrrhizinate is typically at least 0.1% (w/w), suitably 0.1 to 10% (w/w), and preferably 0.2 to 5% (w/w) of the total weight of the composition. In suppositories, and soft gelatin capsules for rectal or vaginal administration the glycyrrhizinate is suitably present in an amount corresponding to between 0.1 g and 2 g per 100 g of composition. Preferably the glycyrrhizinate is present in an amount corresponding to between 0.2 g and 1 g per 100 g.

The compositions can also contain a protease inhibitor, preferably a non-surfactant protease inhibitor, for example as described in EP 127535.

The pH of the compositions of the present invention can vary within a broad range according to the chemicophysical properties of the different ingredients in the compositions. However, suitably the pH of the composition is in the range from pH 3 to 8, preferably from approximately pH 3.5 to approximately pH 7. In order to regulate the pH and maintain a suitable value, a buffering agent may be included in the composition. Examples of buffering agents which may be used include citrates, (for example a mixture of citric acid and sodium citrate), acetates, phosphates and adipates. In addition to a buffering agent such as those described hereinabove, an alkali metal hydroxide e.g. sodium hydroxide may be incorporated to regulate the pH.

For the avoidance of doubt, compositions containing a combination of a calcitonin, a Gelucire, ammonium glycyrrhizinate and benzyl alcohol are specifically excluded from this application, such formulations being described in International application no. WO 93/06854.

In general, the above-mentioned compositions can be made according to well known pharmaceutical procedures, see for example Remington's Pharmaceutical Sciences, 17th Edition, Mack Publishing Company, 1985. Soft gelatin capsules may be prepared for example as described in WO 84/03417 or EPA 122463.

The compositions of the present invention can be used in the treatment of diseases such as Paget's disease (osteitis deformans), osteoporosis including post-menopausal osteoporosis, Sudeck's disease and various hypercalcaemic conditions (see, for example, the Physician's Desk Reference, 42nd Edition, 1988, pages 1796 and 1797).

The quantity of pharmacologically active substance in a unit dose of the compositions of the present invention will vary according to the potency of the calcitonin and the nature of the composition. However, in general, a unit dose of a composition intended for human use typically contains between 1 and 1000 International Units (I.U.) of a calcitonin. For elcatonin, a unit dose in general contains from 5 to 200 I.U. A unit dose adapted for colonic administration preferably contains from 40–800 I.U. of elcatonin. The compositions will be administered to the patient in dosages which contain an amount of calcitonin effective to treat the disease in question. A typical dosage regimen for elcatonin is from 5 to 200 I.U. per day (or 40–800 I.U. for colonic administration) which may be administered in a single dose or in divided doses for example on consecutive or alternate days.

The term "International Unit" refers to the appropriate International Reference Preparation (I.R.P.) of human, salmon or porcine calcitonins, or elcatonin, established by the National Institute for Biological Standards and Control, Blanche Lane, South Mimms, Potters Bar, Hertfordshire, EN6 3QG, United Kingdom.

The invention will now be illustrated in greater detail by the following examples.

Formulations for Vaginal, Rectal or Oral Administration

Example 1

|  | a | b |
|---|---|---|
| Elcatonin (mg) | 7.4, 14.8 | 25, 50 or 100 |
| (6500 I.U./mg potency) | or 29.6 | |
| Polyethylene glycol 600 (g) | 550.0 | 550.0 |
| Gelucire 44/14 ® (g) | 400.0 | 400.0 |
| Distilled water (g) | 44.1 | 49.1 |
| Ammonium glycyrrhizinate (g) | 5.0 | — |
| Sodium chloride (mg) | 300.0 | 300.0 |
| Sodium citrate dihydrate (mg) | 231.5 | 231.5 |
| Sodium hydroxide (mg) | 350 | — |
| Citric acid (mg) | 18.5 | 18.5 |

Method

Mix together the citric acid, sodium citrate dihydrate, sodium chloride, distilled water, elcatonin and if appropriate ammonium glycyrrhizinate and sodium hydroxide in a water bath regulated at a temperature of about 70° C., and then cool to about 55° C. Melt the Gelucire® at about 50° to 60° C., add the polyethylene glycol 600, cool to about 45° to 50° C. and then add the above solution, under stirring.

The Final mixture, cooled to about 30° C., may be filled into soft gelatin capsules for rectal or vaginal administration (1 g formulation (a) each capsule) or into soft gelatin capsules (300 mg formulation (b) per capsule) for oral administration. Optionally, the mixture may be dried under vacuum and filled into hard gelatin capsules (290 mg formulation (b) per capsule) for oral administration. Capsules for oral administration may be coated with the following coating:

|  | mg/capsule |
|---|---|
| Eudragit S | 33.0 |
| Talc | 9.0 |
| Dibutylphthalate | 6.6 |
| PEG 6000 | 0.9 |

Example 2

|  | a | b |
|---|---|---|
| Elcatonin (mg) | 7.4, 14.8 | 25, 50 or 100 |
| (6500 I.U./mg potency) | or 29.6 | |
| Polyethylene glycol 600 (g) | 580.0 | 580.0 |
| Gelucire 44/14 ® (g) | 420.0 | 420.0 |

Method

Melt the Gelucire® at about 50° to 60° C., add the polyethylene glycol, cool to about 45° to 50° C. and add the elcatonin. The mixture may be filled into soft gelatin capsules for rectal, vaginal or oral administration and optionally coated for oral administration as in Example 1. Alternatively for oral administration the mixture may be filled into hard gelatin capsules coated as above.

Example 3

|  | a | b |
|---|---|---|
| Elcatonin (mg) | 7.4, 14.8 | 25, 50 or 100 |
| (6500 I.U./mg potency) | or 29.6 | |
| Gelucire 35/10 (g) | 950.0 | 950.0 |
| Distilled water (g) | 44.1 | 49.1 |
| Ammonium glycyrrhizinate (g) | 5.0 | — |
| Sodium chloride (mg) | 300.0 | 300.0 |
| Sodium citrate dihydrate (mg) | 231.5 | 231.5 |
| Sodium hydroxide (mg) | 350.0 | — |
| Citric acid (mg) | 18.5 | 18.5 |

Method

The formulations are prepared in a similar manner to Example 1, without the inclusion of polyethylene glycol.

Example 4

|  | a | b |
|---|---|---|
| Elcatonin (mg) | 7.4, 14.8 | 25, 50 or 100 |
| (6500 I.U./mg potency) | or 29.6 | |
| Gelucire 35/10 ® (g) | 1000.0 | 1000.0 |

Method

Melt the Gelucire® at about 50° to 60° C., cool to about 45° to 50° C. and add the elcatonin. The mixture may be filled into gelatin capsules and optionally coated as in Examples 1 and 2.

Example 5

|  | a | b |
|---|---|---|
| Elcatonin (mg) | 7.4, 14.8 | 25, 50 or 100 |
| (6500 I.U./mg potency) | or 29.6 | |
| Gelucire 37/02 ® (g) | 950.0 | 950.0 |
| Distilled water (g) | 49.1 | 44.1 |
| Ammonium glycyrrhizinate (g) | — | 5.0 |
| Sodium chloride (mg) | 300.0 | 300.0 |
| Sodium citrate dihydrate (mg) | 231.5 | 231.5 |
| Sodium hydroxide (mg) | — | 350.0 |
| Citric acid (mg) | 18.5 | 18.5 |

Method

The formulations are prepared in a similar manner to Example 1, without the inclusion of polyethylene glycol.

Example 6

|  | a | b |
|---|---|---|
| Elcatonin (mg) | 7.4, 14.8 | 25, 50 or 100 |
| (6500 I.U./mg potency) | or 29.6 | |
| Gelucire 37/02 ® (g) | 1000.0 | 1000.0 |

Method

Melt the Gelucire® at about 50° to 60° C., cool to about 45° to 50° C. and add the elcatonin. The mixture may be filled into gelatin capsules and optionally coated as in Examples 1 and 2.

Example 7

|  | a | b |
|---|---|---|
| Elcatonin (mg) (6500 I.U./mg potency) | 7.4, 14.8 or 29.6 | 25, 50 or 100 |
| Gelucire 44/14 ® (g) | 450.0 | 450.0 |
| Labrafil M2125CS ® (g) | 500.0 | 500.0 |
| Distilled water (g) | 44.1 | 49.1 |
| Ammonium glycyrrhizinate (g) | 5.0 | — |
| Sodium chloride (mg) | 300.0 | 300.0 |
| Sodium citrate dihydrate (mg) | 231.5 | 231.5 |
| Sodium hydroxide (mg) | 350.0 | — |
| Citric acid (mg) | 18.5 | 18.5 |

Method

Melt the Gelucire® at about 50° to 60° C., add the Labrafil®, cool to around 45° to 50° C. and add the buffered elcatonin solution, as in Example 1. The mixture may be filled into capsules as described in Example 1.

Example 8

|  | a | b |
|---|---|---|
| Elcatonin (mg) (6500 I.U./mg potency) | 7.4, 14.8 or 29.6 | 25, 50 or 100 |
| Gelucire 44/14 ® (g) | 500.0 | 500.0 |
| Labrafil M2125CS ® (g) | 500.0 | 500.0 |

Method

Melt the Gelucire® at about 50° to 60° C., add the Labrafil®, cool to about 45° to 50° C. and add the elcatonin with stirring. The mixture may be filled into capsules as described in Examples 1 and 2.

Example 9

|  | a | b |
|---|---|---|
| Elcatonin (mg) (6500 I.U./mg potency) | 7.4, 14.8 29.6 | 25, 50 or 100 |
| Labrasol ® (g) | 950.0 | 950.0 |
| Distilled water (g) | 49.1 | 49.1 |
| Sodium chloride (mg) | 300.0 | 300.0 |
| Sodium citrate dihydrate (mg) | 231.5 | 231.5 |
| Citric acid (mg) | 18.5 | 18.5 |

Method

Prepare the buffered elcatonin solution as in Example 1 and then add the Labrasol® under stirring. The mixture may be filled into capsules as described in Example 1.

Example 10

|  | a | b |
|---|---|---|
| Elcatonin (mg) (6500 I.U./mg potency) | 7.4, 14.8 or 29.6 | 25, 50 or 100 |
| Labrasol ® (g) | 1000.0 | 1000.0 |

Method

Mix the Labrasol® and elcatonin under stirring. The mixture may be filled into capsules as described in Examples 1 and 2.

Example 11

|  | a | b |
|---|---|---|
| Elcatonin (mg) (6500 I.U./mg potency) | 7.4, 14.8 or 29.6 | 25, 50 or 100 |
| Polyethylene glycol 600 (g) | 550.0 | 550.0 |
| Labrasol ® (g) | 400.0 | 400.0 |
| Distilled water (g) | 49.1 | 44.1 |
| Ammonium glycyrrhizinate (g) | — | 5.0 |
| Sodium chloride (mg) | 300.0 | 300.0 |
| Sodium citrate dihydrate (mg) | 231.5 | 231.5 |
| Sodium hydroxide (mg) | — | 350.0 |
| Citric acid (mg) | 18.5 | 18.5 |

Method

Mix the Labrasol® with the polyethylene glycol and add the buffered elactonin solution with stirring. The mixture may be filled into capsules as in Example 1.

Example 12

|  | a | b |
|---|---|---|
| Elcatonin ® (mg) (6500 I.U./mg potency) | 7.4, 14.8 or 29.6 | 25, 50 or 100 |
| Polyethylene glycol, 600 (g) | 580.0 | 580.0 |
| Labrasol (g) | 420.0 | 420.0 |

Method

Analogous to Example 2.

Example 13

|  | a | b |
|---|---|---|
| Elcatonin (mg) (6500 I.U./mg potency) | 7.4, 14.8 or 29.6 | 25, 50 or 100 |
| Labrafil M2125CS ® (g) | 1000.0 | 1000.0 |

Method

Analogous to Example 10.

Example 14

|  | a | b |
|---|---|---|
| Elcatonin (mg) (6500 I.U./mg potency) | 7.4, 14.8 or 29.6 | 25, 50 or 100 |
| Labrafil WL 2609 BS ® (g) | 1000.0 | 1000.0 |

Method

Analogous to Example 10.

Example 15

|  | a | b |
|---|---|---|
| Elcatonin (mg) (6500 I.U./mg potency) | 7.4, 14.8 or 29.6 | 25, 50 or 100 |
| Labrasol ® (g) | 667.0 | 667.0 |
| Gelucire 44/14 ® (g) | 333.0 | 333.0 |

Method

Analogous to Example 8.

Example 16

|  | a | b |
|---|---|---|
| Elcatonin (mg) | 7.4, 14.8 or 29.6 | 25, 50 or 100 |
| (6500 I.U./mg potency) | | |
| Labrafil WL 2609 BS ® (g) | 500.0 | 500.0 |
| Gelucire 35/10 ® (g) | 500.0 | 500.0 |

Method

Analogous to Example 8.

Example 17

|  | a | b |
|---|---|---|
| Elcatonin (mg) | 7.4, 14.8 or 29.6 | 25, 50 or 100 |
| (6500 I.U./mg potency) | | |
| Labrasol ® (g) | 500.0 | 500.0 |
| Gelucire 44/14 ® (g) | 500.0 | 500.0 |

Method

Analogous to Example 8.

Suppository for Rectal or Vaginal Administration

Example 18

| Elcatonin (mg) | 15.4 |
|---|---|
| (6500 I.U./mg potency) | |
| Hard fat (g) | 750.0 |
| Labrafil WL 2514 CS ® (g) | 750.0 |

Method

The hard fat and the Labrafil® are melted and mixed at 50° to 60° C., cooled to 45° to 50° C. and the elcatonin is added with stirring. The mass obtained is poured into suppository moulds and cooled to room temperature, to give suppositories of 1.5 g each.

Solution for Nasal, Sublingual, Buccal, Rectal or Vaginal Administration

Example 19

|  | a | b | c |
|---|---|---|---|
| Elcatonin (mcg) | 3690 | 7380 | 3690 |
| (6500 I.U./mg potency) | | | |
| Gelucire 44/14 ® (g) | 8.0 | 8.0 | 8.0 |
| Polyethylene glycol 600 (g) | 11.0 | 11.0 | 11.0 |
| Citric acid (mg) | 37.0 | 37.0 | 37.0 |
| Sodium citrate dihydrate (mg) | 463.0 | 463.0 | 463.0 |
| Sodium chloride (mg) | 600.0 | 600.0 | 600.0 |
| Benzyl alcohol (g) | 2.0 | — | — |
| Methyl p-hydroxybenzoate (mg) | — | 130.0 | — |
| Propyl p-hydroxybenzoate (mg) | — | 20.0 | — |
| Benzalkonium chloride (mg) | — | — | 10.0 |
| Distilled water | q.s. to 100 ml | | |
| 1N sodium hydroxide | q.s. to pH 6 | | |

Method

All the components except elcatonin are dissolved at about 35° to 40° C., in 80% of the water and the resulting solution cooled to room temperature. The elcatonin is dissolved in the remaining 20% of the water and the two solutions are mixed under stirring. For nasal, sublingual or buccal use the solution may be administered at a volume of 100 μl and for rectal or vaginal administration at 200 to 400 μl.

Dosage Form for Transdermal Administration

Example 20

|  |  |  |
|---|---|---|
| Elcatonin (mg) | 6.0 | 6.0 |
| (6500 I.U./mg potency) | | |
| Gelucire 44/14 ® or 35/10 (g) | 8.0 | 8.0 |
| Polyethylene glycol 600 (g) | 11.0 | 11.0 |
| Ammonium glycyrrhizinate (g) | 2.0 | — |
| Carbopol 934 (g) | 2.0 | 2.0 |
| Citric acid (mg) | 37.0 | 37.0 |
| Sodium citrate dihydrate (mg) | 463.0 | 463.0 |
| Sodium chloride (mg) | 600.0 | 600.0 |
| Distilled water | q.s.to 100 g | |
| 1N NaOH | q.s. to pH 6 | |

Method

The formulation of Example 20 is prepared by mixing together the Gelucire®, polyethylene glycol 600, citric acid, sodium citrate dihydrate, sodium chloride, Carbonyl 934, sodium hydroxide, ammonium glycyrrhizinate (when used) and part of distilled water in a water bath regulated at a temperature of about 70° C. To the resulting gel, cooled to room temperature, a solution of elcatonin in the remaining part of distilled water, is then added. The final gel is filled into patches of 500 mg each.

Formulation for Rectal or Vaginal Administration

Example 21

| Elcatonin (mg) | 14.8 |
|---|---|
| (6500 I.U./mg potency) | |
| Polyethylene glycol 600 (g) | 550.0 |
| Gelucire 44/14 ® (g) | 400.0 |
| Distilled water (g) | 49.449 |
| Sodium chloride (mg) | 300.0 |
| Sodium citrate dihydrate (mg) | 231.5 |
| Citric acid (mg) | 18.5 |
| Sodium hydroxide (mg) | 1.0 |

Method

The citric acid, sodium citrate dihydrate, sodium chloride, sodium hydroxide, distilled water and elactonin, were mixed together in a water bath at a temperature of about 55° C. The Gelucire® was melted at about 50° to 60° C., and the polyethylene glycol 600 added. This mixture was cooled to about 45° to 50° C. and then added to the above solution, under stirring.

The final mixture, cooled to about 30° C., may be filled into soft gelatin capsules (1 g each capsule) for rectal or vaginal administration.

Formulations for Vaginal, Rectal or Oral Administration

Example 22

|  | a | b |
|---|---|---|
| Elcatonin (mg) | 7.4, 14.8 or 29.6 | 50, 100, 200 or 400 |
| (6500 I.U./mg potency) | | |
| Labrasol ® (g) | 500.0 | 500.0 |
| Polyethylene glycol 600 (g) | 398.5 | 398.5 |
| Polyethylene glycol 200 (g) | 100.0 | 100.0 |
| Sodium lauryl sulphate (g) | 1.5 | 1.5 |

Method

Dissolve elcatonin in polyethylene glycol 200, then add and mix together all the other components.

The final mixture may be filled into capsules as described in Example 1.

Example 23

| | |
|---|---|
| Elcatonin (mg) (6500 I.U./mg potency) | 2.55 |
| Labrasol ® (g) | 500.0 |
| Polyethylene glycol 600 (g) | 398.5 |
| Polyethylene glycol 200 (g) | 100.0 |
| Sodium lauryl sulphate (g) | 1.5 |

Method

The formulation of Example 23 was prepared as described in Example 22.

Example 24

| | a | b |
|---|---|---|
| Elcatonin (mg) (6500 I.U./mg potency) | 7.4, 14.8 or 29.6 | 50, 100, 200 or 400 |
| Labrasol ® (g) | 500.0 | 500.0 |
| Polyethylene glycol 600 (g) | 348.5 | 348.5 |
| Polyethylene glycol 200 (g) | 100.0 | 100.0 |
| Sodium lauryl sulphate (g) | 1.5 | 1.5 |
| Distilled water (g) | 44.45 | 44.45 |
| Ammonium glycyrrhizinate (g) | 5.0 | 5.0 |
| Sodium chloride (mg) | 300.0 | 300.0 |
| Sodium citrate dihydrate (mg) | 231.5 | 231.5 |
| Citric acid (mg) | 18.5 | 18.5 |

Method

Mix together the citric acid, sodium citrate dihydrate, sodium chloride, ammonium glycyrrhizinate, distilled water and elcatonin, in a water bath at a temperature of about 55° C. Mix together polyethylene glycol 200, polyethylene glycol 600 and Labrasol®. Blend the two mixtures and cool to room temperature.

The final mixture may be filled into capsules as described in Example 1.

Example 25

| | a | b |
|---|---|---|
| Elcatonin (mg) (6500 I.U./mg potency) | 7.4, 14.8 or 29.6 | 50, 100, 200 or 400 |
| Labrasol ® (g) | 857.0 | 857.0 |
| Polyethylene glycol 200 (g) | 33.0 | 33.0 |
| Sodium lauryl sulphate (g) | 10.0 | 10.0 |
| Distilled water (g) | 50.0 | 50.0 |
| Adipic acid (g) | 40.0 | 40.0 |
| Sodium acetate trihydrate (g) | 10.0 | 10.0 |

Method

Dissolve the elcatonin in polyethylene glycol 200 and distilled water, then add Labrasol®, sodium lauryl sulphate, adipic acid and sodium acetate trihydrate and mix together.

The final mixture may be filled into capsules as described in Example 1.

Trial A

The absorption enhancing property of a polyglycolysed glyceride (Gelucire® 44/14) was demonstrated by the following trial.

The preparation reported in Example 21, containing 40% of Gelucire 44/14, was compared, in a test of pharmacodynamic activity in rabbits i.e. lowering of calcium concentration in the serum, with a reference preparation without Gelucire, having the following composition:

Reference preparation

| | |
|---|---|
| Elcatonin (mg) (6500 I.U./mg potency) | 14.8 |
| Polyethylene glycol 600 (g) | 880.0 |
| Polyethylene glycol 4000 (g) | 70.0 |
| Distilled water (g) | 49.449 |
| Sodium chloride (mg) | 300.0 |
| Sodium citrate dihydrate (mg) | 231.5 |
| Citric acid (mg) | 18.5 |
| Sodium hydroxide (mg) | 1.0 |

(Polyethylene glycol 4000 was added in order to have a viscosity similar to that of the preparation of Example 21; the preparation method is similar to that of Example 21).

The preparations were administered rectally with a small catheter, in the amount of 0.5 g/Kg body weight (corresponding to about 50° I.U./Kg) to groups of 6, conscious, fasted overnight, New Zealand rabbits, weighing about 2 Kg.

Serum calcium concentration was measured (with an atomic absorption spectrophotometer VARIAN 30/40) on blood samples obtained in each animal, from the lateral vein of ear, 0, 60, 120, 180 and 240 min after administration of the products.

The results, expressed as residual percentage of sen calcium concentration as compared with baseline values (0 time), are reported in Table 1.

TABLE 1

| | Residual percentage of serum calcium as compared with baseline values (mean values ± standard errors) | | | | |
|---|---|---|---|---|---|
| | 0 min | 60 min | 120 min | 180 min | 240 min |
| Preparation of Example 21 | 100.0 | 77.2 ± 2.5 | 81.6 ± 2.6 | 92.8 ± 1.3 | 94.7 ± 1.3 |
| Reference preparation without Gelucire ® | 100.0 | 83.7 ± 2.8 | 93.9 ± 1.1 | 95.1 ± 2.6 | 97.5 ± 3.6 |

Trial B

The absorption enhancing property of a polyglycolysed glyceride (Labrasol®) is demonstrated by this trial.

The preparation reported in Example 23, containing 50% of Labrasol®, was compared, in a test of pharmacodynamic activity in rats i.e. lowering of calcium concentration in the serum, with a reference preparation without Labrasol® (Labrasol® was completely substituted by polyethylene glycol 600).

The preparations were administered intracolonically with a small catheter, in the volume of 2 ml/Kg body weight (corresponding to about 30 I.U./Kg) to groups of 4, conscious, fasted overnight, Sprague Dawley rats, weighing about 220±220 g.

Serum calcium concentration was measure (with an atomic absorption spectrophotometer VARIAN 30/40) on blood samples obtained in each animal, from the caudal vein, 0, 60 and 120 min after administration of the products.

The results, expressed as a residual percentage of serum calcium concentration as compared with baseline values (0 time) are reported in Table 2.

TABLE 2

| | Residual percentage of serum calcium as compared with baseline values (mean values ± standard errors) | | |
|---|---|---|---|
| | 0 min | 60 min | 120 min |
| Preparation of Example 23 | 100.0 | 79.5 ± 3.0 | 88.2 ± 5.8 |
| Reference preparation without Labrasol ® | 100.0 | 96.0 ± 2.5 | 99.1 ± 1.4 |

We claim:

1. A pharmaceutical composition adapted for rectal, vaginal, nasal, sublingual, buccal, oral, transdermal, or colonic administration which composition comprises a calcitonin and a saturated polyglycolysed glyceride in a solid or semisolid dosage form.

2. A composition according to claim 1 wherein the saturated polyglycolysed glyceride consists of $C_8$-$C_{18}$ glycerides and polyethylene glycol esters.

3. A composition according to claim 1 wherein the saturated polyglycolysed glyceride contains $C_8$-$C_{10}$ glycerides.

4. The composition according to claim 3 wherein the polyglycolysed glyceride is selected from GELUCIRE 44/14 and LABRASOL.

5. A composition according to claim 1 which comprises a controlled release delivery form adapted for oral administration and subsequent release of the active ingredient in the region of the colonic mucosa.

6. A composition according to claims 1 in the form of a unit dose which contains from 1 to 1000 I.U. of a calcitonin.

7. A composition according to claims 1 which has a pH in the range from approximately 3.5 to approximately 7.

8. A method of treating osteoporosis, in a human in need thereof which method comprises administering to said human an effective amount of a composition according to claim 1.

9. The method according to claim 8 wherein the compound is administered orally, nasally, sublingual, buccal, transdermally, vaginally or rectally.

10. The method according to claim 8 wherein the polyglycolysed glyceride is selected from GELUCIRE 44/14 and LABRASOL.

11. A method of enhancing the transdermal or transmucosal absorption of a calcitonin in a mammal in need thereof, which method comprises co-administering to said mammal with the calcitonin an effective amount of an absorption enhancer which is a saturated polyglycolysed glyceride.

12. The method according to claims 11 wherein the saturated polyglycolysed glyceride consists of $C_8$-$C_{18}$ glycerides and polyethylene glycol esters.

13. The method according to claim 12 wherein the polyglycolysed glyceride consists of $C_8$-$C_{10}$ glycerides.

14. The method according to claim 11 wherein the polyglycolysed glyceride is selected from GELUCIRE 35/10, 37/02, or 44/14, WL 2514CS and LABRASOL.

15. The method according to claim 11 wherein the calcitonin is elcatonin.

16. The method according to claim 11 wherein the calcitonin and absorption enhancer are administered in the form of a unit dose which contains from 1 to 1000 I.U. of calcitonin.

17. A pharmaceutical composition adapted for rectal or vaginal administration which composition comprises a calcitonin and a saturated polyglycolysed glyceride, in a solid suppository or soft gelatin capsule dosage form.

18. The composition according to claim 17 wherein the saturated polyglycolysed glyceride contains $C_8$-$C_{10}$ glycerides.

19. The composition according to claim 18 wherein the dosage form contains from 1 to 1000 I.U. of a calcitonin.

20. The composition according to claim 19 wherein the calcitonin is elcatonin.

21. The method according to claim 17 wherein the polyglycolysed glyceride is selected from GELUCIRE 35/10, 37/02, or 44/14, WL 2514CS and LABRASOL.

* * * * *